United States Patent [19]

Bartmann et al.

[11] Patent Number: 5,458,806

[45] Date of Patent: Oct. 17, 1995

[54] FLUOROMETHYL KETONES AND LIQUID-CRYSTALLINE MEDIA

[75] Inventors: Ekkehard Bartmann, Erzhausen; Herbert Plach, Darmstadt, both of Germany

[73] Assignee: Merck Patent Gesellschaft Mit Beschrankter Haftung, Darmstadt, Germany

[21] Appl. No.: 238,087

[22] Filed: May 4, 1994

[30] Foreign Application Priority Data

May 5, 1993 [DE] Germany ............... 43 14 872.7
May 5, 1993 [DE] Germany ............... 43 01 699.5

[51] Int. Cl.$^6$ ............... C09K 19/30; C09K 19/12; C07C 49/213; C07C 19/08
[52] U.S. Cl. ............... 252/299.63; 252/299.66; 252/299.61; 252/299.62; 568/308; 568/335; 544/298; 549/369; 549/370; 570/129; 570/144; 560/100; 560/102; 560/65
[58] Field of Search ............... 252/299.63, 299.66, 252/299.62, 299.61; 544/298; 549/369, 370; 570/129, 144; 546/339; 560/65, 100, 102; 568/308, 335

[56] References Cited

U.S. PATENT DOCUMENTS

| | | | |
|---|---|---|---|
| 4,330,426 | 5/1982 | Eidenschink et al. | 252/299.63 |
| 4,382,012 | 5/1983 | Eidenschink et al. | 252/299.1 |
| 4,886,619 | 12/1989 | Janulis | 252/299.1 |
| 5,045,229 | 9/1991 | Bartmann et al. | 252/299.01 |
| 5,190,688 | 3/1993 | Sage et al. | 252/299.01 |
| 5,196,140 | 3/1993 | Poetsch et al. | 252/299.6 |
| 5,198,151 | 3/1993 | Kuratate et al. | 252/299.66 |
| 5,262,082 | 11/1993 | Janulis et al. | 252/299.01 |
| 5,262,085 | 11/1993 | Bartmann et al. | 252/299.63 |
| 5,348,677 | 9/1994 | Poetsch et al. | 252/299.6 |

*Primary Examiner*—Cynthia Harris

*Attorney, Agent, or Firm*—Millen, White, Zelano & Branigan

[57] ABSTRACT

Fluoromethyl ketones of the formula I

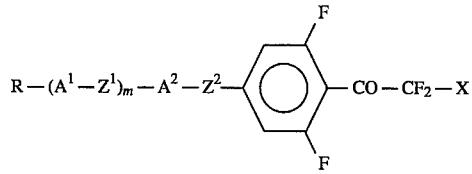

are suitable as components of liquid-crystalline media wherein R is H, a substituted or unsubstituted alkyl or alkenyl radical having 1 to 15 carbon atoms, $A^1$ and $A^2$ are each, independently of one another, a
(a) trans-1,4-cyclohexylene radicals and derivatives thereof in which, in addition, one or more non-adjacent $CH_2$ groups is optionally replaced by —O— and/or —S—,
(b) 1,4-phenylene radicals and derivatives thereof in which, in addition, one or two CH groups is optionally replaced by N, or
(c) radical from the group consisting of 1,4-cyclohexenylene, 1,4-bicyclo(2,2,2)octylene, piperidine-1,4-diyl, naphthalene-2,6-diyl, decahydronaphthalene-2,6-diyl and 1,2,3,4-tetrahydronaphthalene-2,6-diyl, wherein radicals (a) and (b) are optionally substituted by one or two fluorine atoms, $Z^1$ and $Z^2$ are each, independently of one another, —CO—O—, —O—CO—, —$CH_2$O—, —O$CH_2$—, —$CH_2CH_2$—, —CH=CH—, —C≡C— or a single bond, and one of the radicals $Z^1$ and $Z^2$ is optionally —$(CH_2)_4$— or —CH=CH—$CH_2CH_2$—, X is H, F or Cl and is 0, 1 or 2.

11 Claims, No Drawings

FLUOROMETHYL KETONES AND LIQUID-CRYSTALLINE MEDIA

BACKGROUND OF THE INVENTION

The invention relates to novel fluoromethyl ketones of the formula I

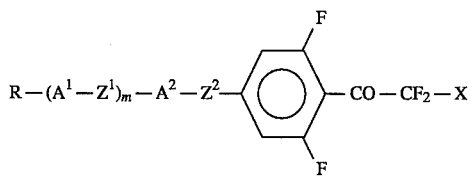

in which is H, an alkyl or alkenyl radical having 1 to 15 carbon atoms which is unsubstituted, monosubstituted by CN or $CF_3$ or at least monosubstituted by halogen, it also being possible for one or more $CH_2$ groups in these radicals to be replaced, in each case independently of one another by —O—, —S—,

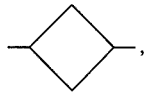

—CO—, —CO—O—, —O—CO— or —O—CO—O—, in such a way that O atoms are not linked directly to one another, $A^1$ and $A^2$ are each, independently of one another, a
  (a) trans-1,4-cyclohexylene radical in which, in addition, one or more non-adjacent $CH_2$ groups may be replaced by —O— and/or —S—,
  (b) 1,4-phenylene radical in which, in addition, one or two CH groups may be replaced by N, or
  (c) radical from the group consisting of 1,4-cyclohexenylene, 1,4-bicyclo(2,2,2)-octylene, piperidine-1,4-diyl, naphthalene-2,6-diyl, decahydronaphthalene-2,6-diyl and 1,2,3,4-tetrahydronaphthalene-2,6-diyl, it being possible for the radicals (a) and (b) to be substituted by one or two fluorine atoms.

$Z^1$ and $Z^2$ are each, independently of one another, —CO—O—, —O—CO—, —$CH_2$O—, —O$CH_2$—, —$CH_2CH_2$—, —CH=CH—, —C≡C— or a single bond, and one of the radicals $Z^1$ and $Z^2$ is alternatively —$(CH_2)_4$— or —CH=CH—$CH_2CH_2$—, is H, F or Cl and is 0, 1 or 2.

The invention furthermore relates to the use of these compounds as components of liquid-crystalline media, and to liquid-crystal and electro-optical display elements containing the liquid-crystalline media according to the invention.

The compounds of the formula I can be used as components of liquid-crystalline media, in particular for displays based on the principle of the twisted cell, the guest-host effect, the effect of deformation of aligned phases or the effect of dynamic scattering.

SUMMARY OF THE INVENTION

The invention had the object of finding novel, stable, liquid-crystalline or mesogenic compounds which are suitable as components of liquid-crystalline media and, in particular, simultaneously have comparatively low viscosity and relatively high dielectric anisotropy.

It has now been found that compounds of the formula I are eminently suitable as components of liquid-crystalline media. In particular, they have comparatively low viscosities. They can be used to obtain stable, liquid-crystalline media having a broad mesophase range and advantageous values for the optical and dielectric anisotropy. These media furthermore have very good low-temperature behavior and extremely low threshold voltages.

DE 41 01 600 A1 mentions compounds containing a terminal CO—$CF_2$-alkyl group, such as, for example,

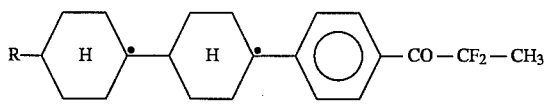

Compounds of the formulae

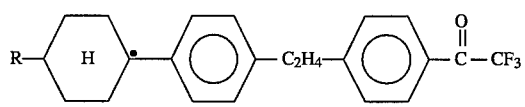

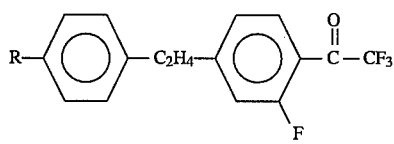

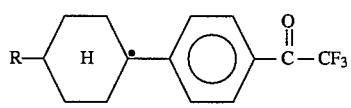

are described in DE-A 40 06 921.

These compounds are in most cases not I/V-stable and are therefore not so suitable for practical applications.

However, with respect to the very wide variety of areas of application of such compounds, it was desirable to have available further UV-stable compounds of high nematogeneity which have properties precisely customized to the particular applications.

In addition, the provision of the compounds of the formula I very generally considerably broadens the range of liquid-crystalline substances which are suitable from various applicational points of view for the preparation of liquid-crystalline mixtures.

The compounds of the formula I have a broad range of applications. Depending on the choice of substituents, these compounds can be used as base materials from which liquid-crystalline media are predominantly composed; however, it is also possible to add compounds of the formula I to liquid-crystalline base materials from other classes of compounds in order, for example, to modify the dielectric and/or optical anisotropy of a dielectric of this type and/or to optimize its threshold voltage and/or its viscosity.

In the pure state, the compounds of the formula I are colorless and form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media containing at least one compound of the formula I and to liquid-crystalline display elements, in particular electro-optical display elements, which contain such media.

For reasons of simplicity below, Y is CO—CF$_2$—X,

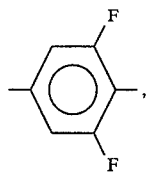

Cyc is a 1,4-cyclohexyl radical, Che is a 1,4-cyclohexenylene radical, Dio is a 1,3-dioxane-2,5-diyl radical, Dit is a 1,3-dithiane-2,5-diyl radical, Phe is a 1,4-phenylene radical, Pyd is a pyridine-2,5-diyl radical, Pyr is a pyrimidine-2,5-diyl radical and Bi is a bicyclo(2,2,2)octylene radical, it being possible for Cyc and/or Phe to be unsubstituted or monosubstituted or disubstituted by F or CN.

A$^1$ and A$^2$ are preferably selected from the group consisting of Cyc, Che, Phe, Pyr, Pyd and Dio, it being preferred if only one of the radicals A$^1$ and A$^2$ present in the molecule is Che, Phe, Pyr, Pyd or Dio.

R is preferably alkyl, furthermore alkoxy. X is preferably F or Cl, in particular F.

The compounds of the formula I accordingly embrace bicyclic compounds of the sub-formulae Ia and Ib:

| | |
|---|---|
| R—A$^2$—A$^3$—Y | Ia |
| R—A$^2$—Z$^2$—A$^3$—Y | Ib | tricyclic compounds of the sub-formulae Ic to If:

| | |
|---|---|
| R—A$^1$—A$^2$—A$^3$—Y | Ic |
| R—A$^1$—Z$^1$—A$^2$—Z$^2$—A$^3$—Y | Id |
| R—A$^1$—Z$^1$—A$^2$—A$^3$—Y | Ie |
| R—A$^1$—A$^2$—Z$^2$—A$^3$—Y | If | and tetracyclic compounds of the sub-formulae Ig to Im:

| | |
|---|---|
| R—A$^1$—A$^1$—A$^2$—A$^3$—Y | Ig |
| R—A$^1$—Z$^1$—A$^1$—A$^2$—A$^3$—Y | Ih |
| R—A$^1$—A$^1$—Z$^1$—A$^2$—A$^3$—Y | Ii |
| R—A$^1$—A$^1$—A$^2$—Z$^2$—A$^3$—Y | Ij |
| R—A$^1$—Z$^1$—A$^1$—Z$^1$—A$^2$—A$^3$—Y | Ik |
| R—A$^1$—A$^1$—Z$^1$—A$^2$—Z$^2$—A$^3$—Y | Il |
| R—A$^1$—Z$^1$—A$^1$—Z$^1$—A$^2$—Z$^2$A$^3$—Y | Im |

Of these, particular preference is given to those of the sub-formulae Ia, Ib, Ic, Id, Ie, If, Ii and Il.

The preferred compounds of the sub- formula Ia embrace those of the sub-formulae Iaa to Iag:

| | |
|---|---|
| R—Phe—A$^3$—Y | Iaa |
| R—Dit—A$^3$—Y | Iab |
| R—Dio—A$^3$—Y | Iac |
| R—Pyr—A$^3$—Y | Iad |
| R—Pyd—A$^3$—Y | Iae |
| R—Cyc—A$^3$—Y | Iaf |
| R—Che—A$^3$—Y | Iag |

Of these, particular preference is given to those of the formulae Iaa, Iad, Iae and Iaf.

The preferred compounds of the sub-formula Ib embrace those of the sub-formulae Iba to Ibc:

| | |
|---|---|
| R—Cyc—CH$_2$CH$_2$—A$^3$—Y | Iba |
| R—Cyc—COO—A$^3$—Y | Ibb |
| R—Phe—COO—A$^3$—Y | Ibc |

The preferred compounds of the sub-formula Ic embrace those of the sub-formulae Ica to Icn:

| | |
|---|---|
| R—Phe—Phe—A$^3$—Y | Ica |
| R—Phe—Pyd—A$^3$—Y | Icb |
| R—Phe—Dio—A$^3$—Y | Icc |
| R—Cyc—Cyc—A$^3$—Y | Icd |
| R—Phe—Cyc—A$^3$—Y | Ice |
| R—Cyc—Pyd—A$^3$—Y | Icf |
| R—Pyd—Phe—A$^3$—Y | Icg |
| R—Pyr—Phe—A$^3$—Y | Ich |
| R—Phe—Pyr—A$^3$—Y | Ici |
| R—Cyc—Pyr—A$^3$—Y | Icj |
| R—Cyc—Phe—A$^3$—Y | Ick |
| R—Dio—Phe—A$^3$—Y | Icl |
| R—Che—Phe—A$^3$—Y | Icm |
| R—Phe—Che—A$^3$—Y | Icn |

Of these, particular preference is given to those of the formulae Ica, Icb, Icd, Ice, Ich, Ici and Ick.

The preferred compounds of the sub-formula Id embrace those of the sub-formulae Ida to Idk:

| | |
|---|---|
| R—Phe—Z$^1$—Phe—Z$^2$—A$^3$—Y | Ida |
| R—Phe—Z$^1$—Dio—Z$^2$—A$^3$—Y | Idb |
| R—Cyc—Z$^1$—Cyc—Z$^2$—A$^3$—Y | Idc |
| R—Cyc—Z$^1$—Pyr—Z$^3$—A$^3$—Y | Idd |
| R—Pyd—Z$^1$—Phe—Z$^2$—A$^3$—Y | Ide |
| R—Phe—Z$^1$—Pyd—Z$^2$—A$^3$—Y | Idf |
| R—Pyr—Z$^1$—Phe—Z$^2$—A$^3$—Y | Idg |
| R—Phe—Z$^1$—Pyr—Z$^2$—A$^3$—Y | Idh |
| R—Phe—Z$^1$—Cyc—Z$^2$—A$^3$—Y | Idi |
| R—Cyc—Z$^1$—Phe—Z$^2$—A$^3$—Y | Idj |
| R—Dio—Z$^1$—Phe—Z$^2$—A$^3$—Y | Idk |

The preferred compounds of the sub-formula Ie embrace those of the sub-formulae Iea to Iej:

| | |
|---|---|
| R—Pyr—Z$^1$—Phe—A$^3$—Y | Iea |
| R—Dio—Z$^1$—Phe—A$^3$—Y | Ieb |
| R—Phe—Z$^1$—Phe—A$^3$—Y | Iec |
| R—Cyc—Z$^1$—Phe—A$^3$—Y | Ied |
| R—Phe—Z$^1$—Cyc—A$^3$—Y | Iee |
| R—Cyc—Z$^1$—Cyc—A$^3$—Y | Ief |
| R—Phe—Z$^1$—Dio—A$^3$—Y | Ieg |
| R—Pyd—Z$^1$—Phe—A$^3$—Y | Ieh |
| R—Phe—Z$^1$—Pyr—A$^3$—Y | Iei |
| R—Cyc—Z$^1$—Pyr—A$^3$—Y | Iej |

The preferred compounds of the sub-formula If embrace those of the sub-formulae Ifa to Ifn:

| | |
|---|---|
| R—Pyr—Phe—Z$^2$—A$^3$—Y | Ifa |
| R—Pyr—Phe—OCH$_2$—A$^3$Y | Ifb |
| R—Phe—Phe—Z$^2$—A$^3$—Y | Ifc |
| R—Phe—Phe—OOC—A$^3$—Y | Ifd |
| R—Cyc—Cyc—Z$^2$—A$^3$—Y | Ife |
| R—Cyc—Cyc—CH$_2$CH$_2$—A$^3$—Y | Iff |
| R—Pyd—Phe—Z$^2$—A$^3$—Y | Ifg |
| R—Dio—Phe—Z$^2$—A$^3$—Y | Ifh |
| R—Phe—Cyc—Z$^2$—A$^3$—Y | Ifi |
| R—Phe—Pyd—Z$^2$—A$^2$—Y | Ifj |
| R—Che—Phe—Z$^2$—A$^3$—Y | Ifk |
| R—Phe—Che—Z$^2$—A$^3$—Y | Ifl |
| R—Cyc—Phe—Z$^2$—A$^3$—Y | Ifm |
| R—Cyc—Phe—OOC—A$^3$—Y | Ifn |

Preference is also given to compounds of the formula I and all of the sub-formulae in which A$^1$ and/or A$^2$ are 1,4-phenylene which is monosubstituted or disubstituted by F or monosubstituted by CN. In particular, these are 2-fluoro-1,4-phenylene, 3-fluoro-1,4-phenylene and 3,5-difluoro-1,4-phenylene, and 2-cyano-1,4-phenylene and 3-cyano-1,4-phenylene. In a particularly preferred embodiment, A$^2$ is 3,5-difluoro-1,4-phenylene and m is 1 or 2.

Z$^1$ and Z$^2$ are preferably a single bond, —CO—O—, —O—CO— or —CH$_2$CH$_2$—, secondarily preferably —CH$_2$O— or —OCH$_2$—.

If one of the radicals $Z^1$ and $Z^2$ is —(CH$_2$)$_4$— or —CH=CH—CH$_2$CH$_2$—, the other radical $Z^1$ or $Z^2$ (if present) is preferably a single bond.

If R is an alkyl radical and/or an alkoxy radical, this may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxyethyl), 2- (=ethoxyethyl) or 3-oxabutyl (=2-methoxyethyl), 2-, 3-or 4-oxapentyl, 2-, 3-, 4- or 5-oxahexyl, 2-, 3-, 4-, 5- or 6-oxaheptyl, 2-, 3-, 4-, 5 -, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R is an alkyl radical in which one CH$_2$ group has been replaced by —CH=CH—, this may be straight-chain or branched. It is preferably straight-chain and has 2 to 10 carbon atoms. It is accordingly in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If R is an alkyl radical in which one CH$_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 carbon atoms.

They are accordingly in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R is an alkyl radical in which one CH$_2$ group has been replaced by unsubstituted or substituted-CH=CH— and an adjacent CH$_2$ group has been replaced by CO or CO—O or O—CO, this may be straight-chain or branched. It is preferably straight-chain and has 4 to 13 carbon atoms. It is accordingly in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If R is an alkyl or alkenyl radical which is monosubstituted by CN or CF$_3$, this radical is preferably straight-chain and the substitution by CN or CF$_3$ is in the ω-position.

If R is an alkyl or alkenyl radical which is at least monosubstituted by halogen, this radical is preferably straight-chain and halogen is preferably F or Cl. In the case of multiple substitution, halogen is preferably F. The resulting radicals also include perfluorinated radicals. In the case of monosubstitution, the fluorine or chlorine substituent may be in any desired position, but is preferably in the ω-position.

Compounds of the formula I containing branched wing groups R may occasionally be of importance due to better solubility in the customary liquid-crystalline base materials, but in particular as chiral dopes if they are optically active. Smectic compounds of this type are suitable as components of ferroelectric materials.

Compounds of the formula I having $S_A$ phases are suitable, for example, for thermally addressed displays.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1methylheptoxy.

If R is an alkyl radical in which two or more CH$_2$ groups have been replaced by —O— and/or —CO—O—, this may be straight-chain or branched. It is preferably branched and has 3 to 12 carbon atoms. It is accordingly in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis (methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl or 5,5-bis(ethoxycarbonyl)hexyl.

Compounds of the formula I which contain wing groups R which are suitable for polycondensation are suitable for the preparation of liquid-crystalline polycondensates.

The formula I covers the racemates of these compounds and the optical antipodes, and mixtures thereof.

Of these compounds of the formula I and of the sub-formulae, those are preferred in which at least one of the radicals present therein has one of the preferred meanings indicated.

In the compounds of the formula I, the stereo-isomers in which the rings Cyc and piperidine are trans-1,4-disubstituted are preferred. Those of the abovementioned formulae which contain one or more Pyd, Pyr and/or Dio groups in each case include the two 2,5-positional isomers.

Some very particularly preferred smaller groups of compounds are those of the sub-formulae I1 to I20:

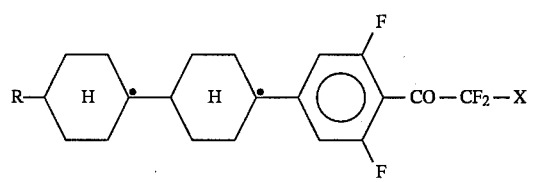 I1
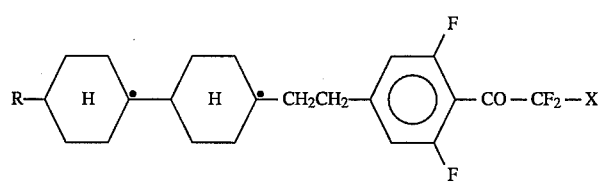 I2
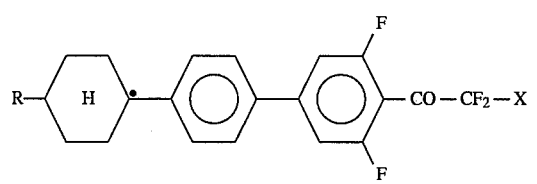 I3
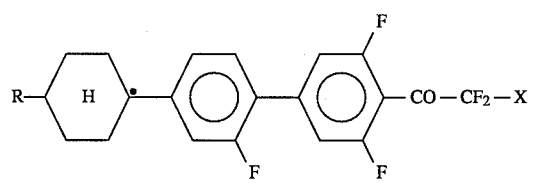 I4
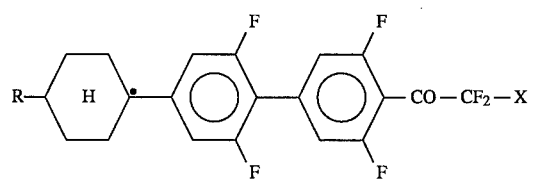 I5
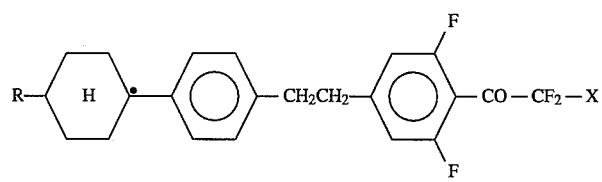 I6
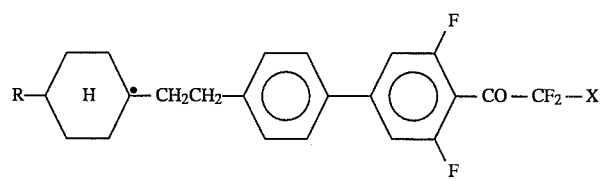 I7
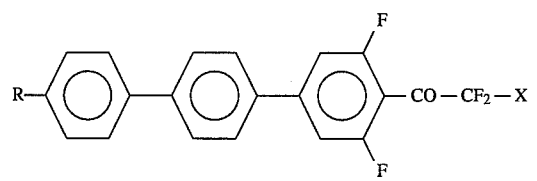 I8
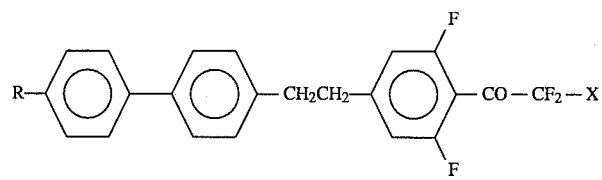 I9

-continued
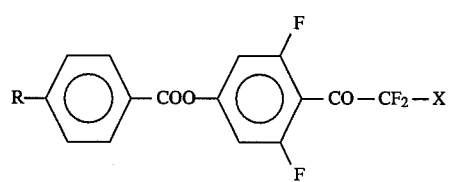
I10
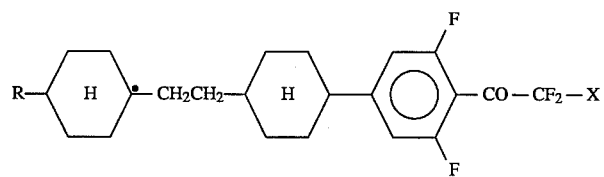
I11
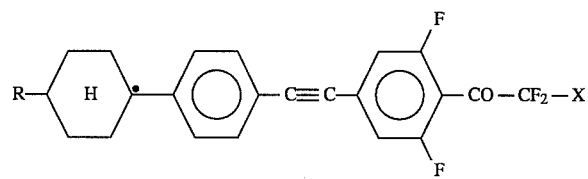
I12
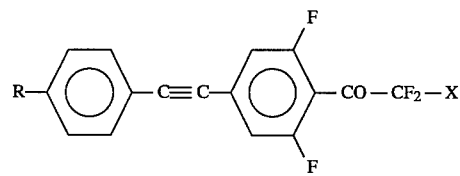
I13
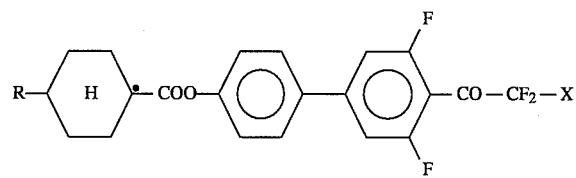
I14
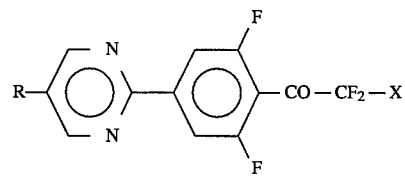
I15
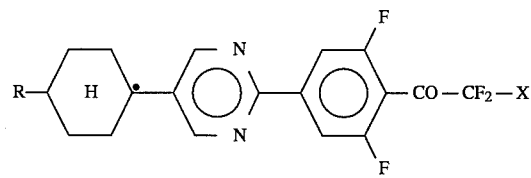
I16
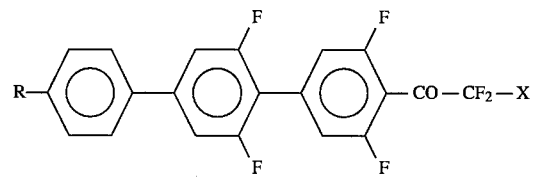
I17

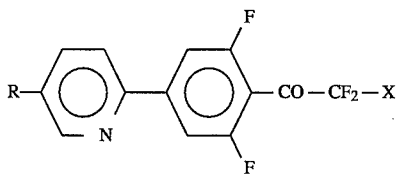

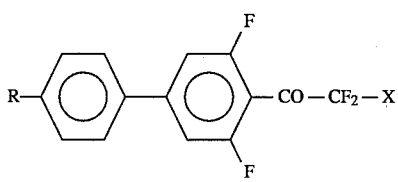

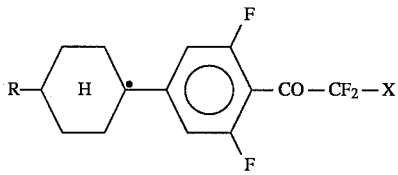

The 1,4-cyclohexenylene group preferably has the following structures:

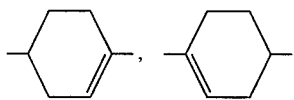

The compounds of the formula I are prepared by methods known per se, as described in the literature (for example in the standard works, such as Houben-Weyl, Methoden der Organischen Chemie, Georg-Thieme-Verlag, Stuttgart), to be precise under reaction conditions which are known and suitable for said reactions.

Use may also be made here of variants which are known per se, but are not described here in greater detail.

The compounds according to the invention can be prepared, for example, by metallating a compound of formula II

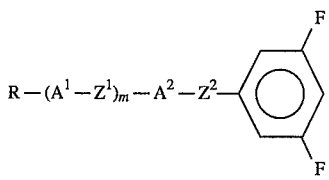

in which R, $A^1$, $A^2$, $Z^1$, $Z^2$ and m are as defined above, in accordance with the reaction scheme below, and reacting the product with methyl 2,2,2-trifluoro- or 2,2-difluoro-2-chloroacetate.

Scheme 1

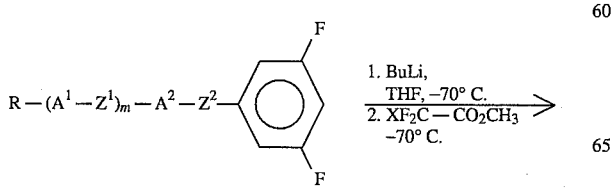

-continued
Scheme 1

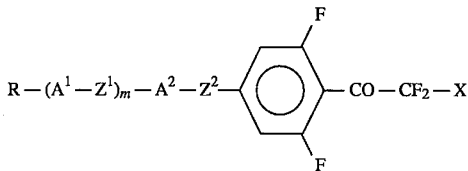

Further synthetic methods are evident to the person skilled in the art. For example, appropriately 5-substituted 1,3-difluorobenzene compounds can be converted into the 1,3-difluoro compounds (L=H) in accordance with the above scheme, and the radical R—$(A^1$—$Z^1)_m$—$A^2$—$Z^2$ can subsequently be introduced by reactions which are customary in liquid-crystal chemistry (for example coupling, for example as described in the article by E. Poetsch, Kontakte (Darmstadt), 1988 (2), p. 15).

The compounds of the formula II can be prepared, for example, in accordance with the synthetic schemes below:

Scheme 2

$(A = -(A^1-Z^1)_m - A^2 -/Z^2 = -CH_2CH_2 -)$

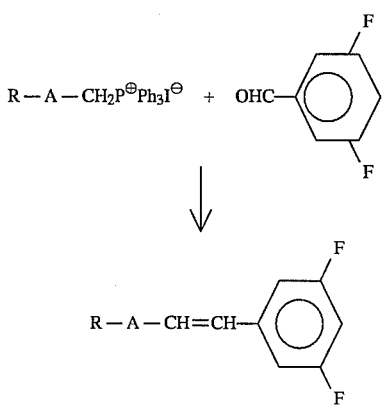

Scheme 2 (continued)

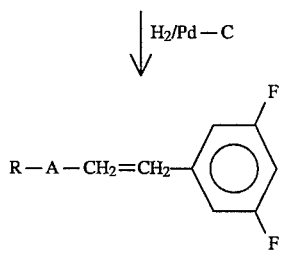

Scheme 3

$(A = -(A^1-Z^1)_m-A^2-/Z^2 = \text{Single bond})$

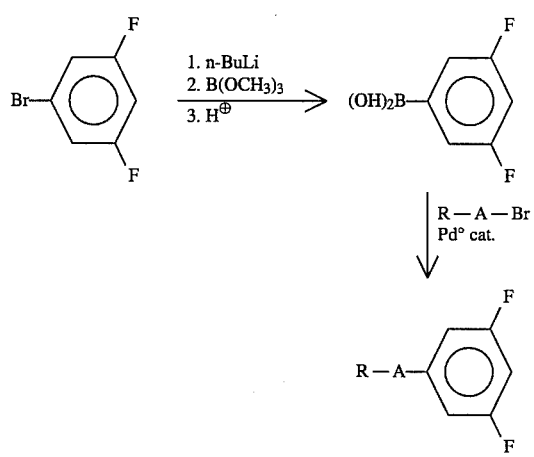

Scheme 4

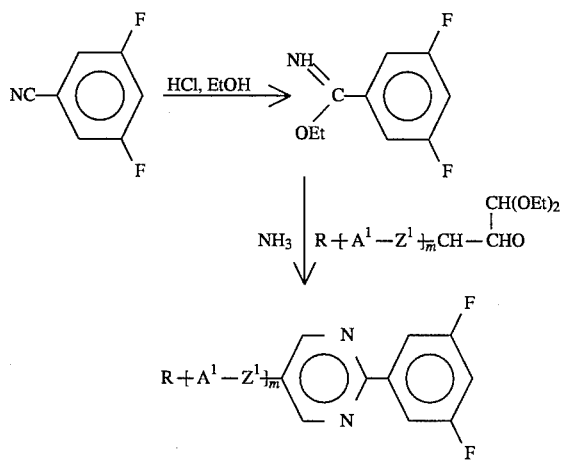

Scheme 5

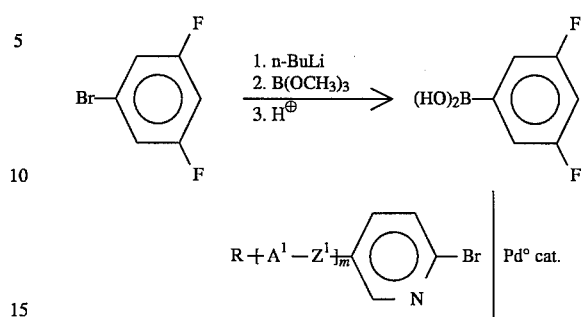

Scheme 6

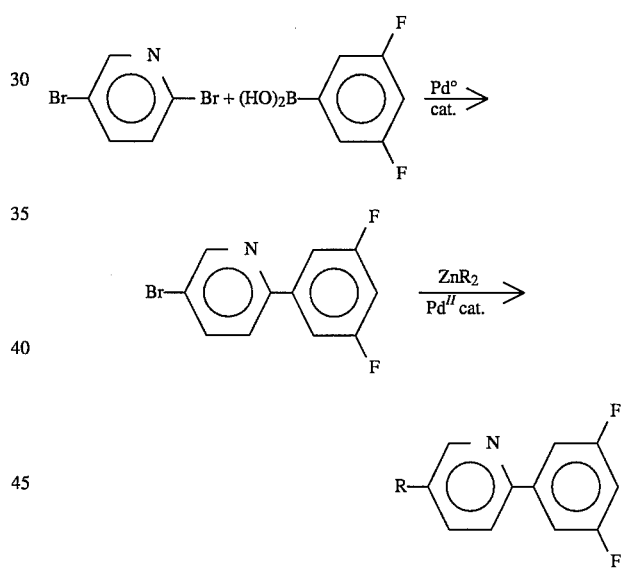

Esters of the formula I can also be obtained by esterifying corresponding carboxylic acids (or reactive derivatives thereof) using alcohols or phenols (or reactive derivatives thereof) or by the DCC method (DCC=dicyclohexylcarbodiimide).

The corresponding carboxylic acids and alcohols or phenols are known or can be prepared analogously to known processes.

In a further process for the preparation of the compounds of the formula I, an aryl halide is reacted with an olefin in the presence of a tertiary amine and in the presence of a palladium catalyst (cf. R. F. Heck, Acc. Chem. Res. 12 (1979) 146). Examples of suitable aryl halides are chlorides, bromides and iodides, in particular bromides and iodides. The tertiary amines necessary for the success of the coupling reaction, such as, for example, triethylamine, are also suitable as solvent. Examples of suitable palladium catalysts are palladium salts, in particular Pd(II) acetate, with organophosphorus(III) compounds, such as, for example, triarylphosphines. The reaction can be carried out in the presence or absence of an inert solvent at temperatures between about 0° and 150°, preferably between 20° and 100°; examples of suitable solvents are nitriles, such as acetonitrile, or hydrocarbons, such as benzene or toluene. The aryl halides and olefins employed as starting materials are in many cases commercially available or can be prepared by processes known from the literature, for example by halogenation of corresponding parent compounds or by elimination reactions on corresponding alcohols or halides.

Ethers of the formula I are obtainable by etherifying the corresponding hydroxyl compounds, preferably corresponding phenols, the hydroxyl compound expediently first being converted into a corresponding metal derivative, for example into the corresponding alkali metal alkoxide or alkali metal phenoxide by treatment with NaH, NaNH$_2$, NaOH, KOH, Na$_2$CO$_3$ or K$_2$CO$_3$. This can then be reacted with the corresponding alkyl halide, alkyl sulphonate or dialkyl sulphate, expediently in an inert solvent, such as, for example, acetone, 1,2-dimethoxyethane, DMF or dimethyl sulphoxide, or alternatively with an excess of aqueous or aqueous-alcoholic NaOH or KOH, at temperatures between about 20° and 100° C.

The starting materials are either known or can be prepared analogously to known compounds.

The compounds of the formula I where $Z^2=-(CH_2)_4-$ can be prepared in accordance with the following scheme:

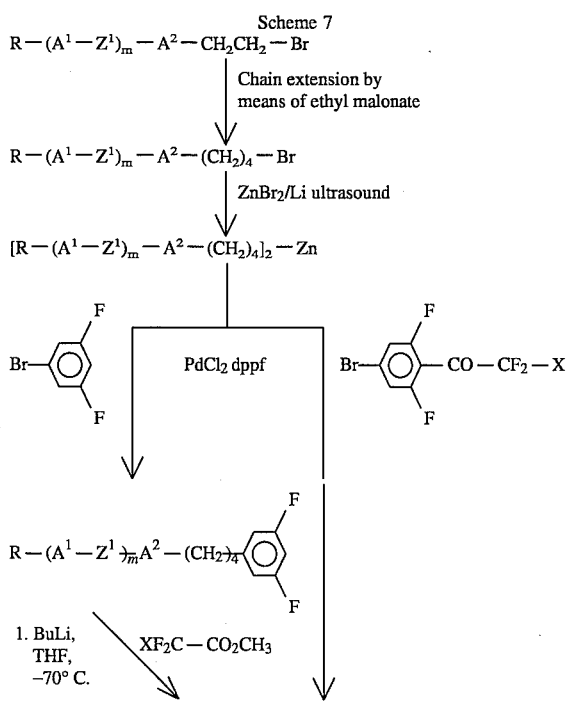

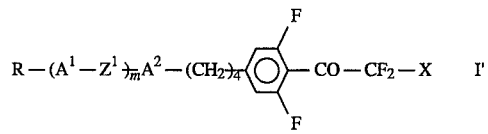

In the Pd(II)-catalyzed coupling reaction, either the target product I' is formed directly or a precursor is formed into which the radical —Y is introduced entirely analogously to the above methods for compounds of the formula I.

The compounds of the formula I' where $Z^2=-CH=CH-CH_2CH_2-$ can be prepared by the Wittig method in accordance with the following scheme:

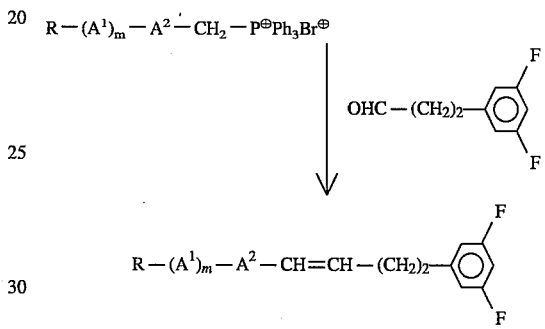

The synthesis of some particularly preferred compounds is shown in greater detail below:

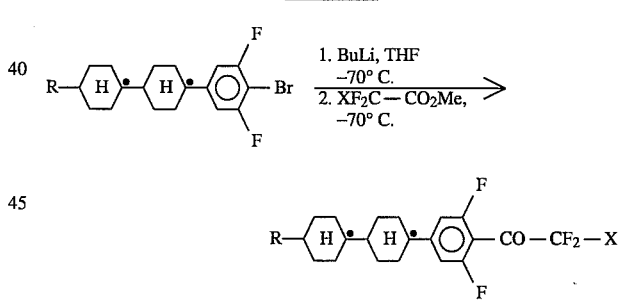

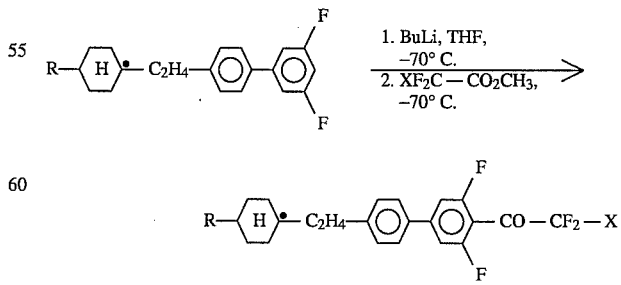

Scheme 11

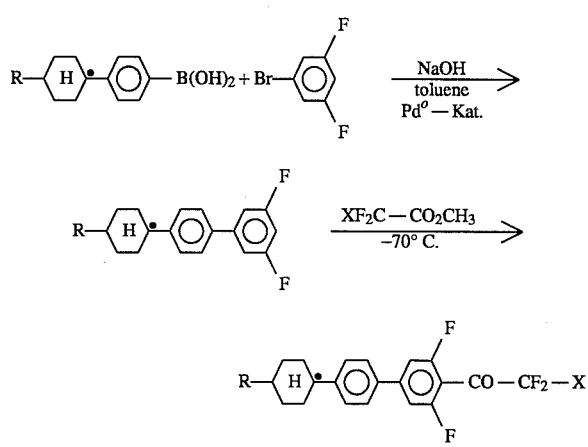

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH$_2$CH$_2$—E—R" | 4 |
| R'—L—C≡C—E—R" | 5 |

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group comprising -Phe-Cyc-, -Cyc-Cyc-, -G-Phe- and -G-Cyc-.

In a smaller sub-group of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5 which is known as group B, R" is —F, —Cl, —NCS or —(O)$_i$CH$_{3-(k+1)}$F$_k$Cl$_l$, where i is 0 or 1, and k+l is 1, 2 or 3; the compounds in which R" has this meaning are labelled with the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$. In the case of a 4-substituted benzene ring, H can be substituted by F in one or both ortho-positions.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is known as group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a –5a and is preferably alkyl, alkoxy or alkenyl. In the case of a 4-substituted benzene ring, H can be substituted by F in one or both ortho-positions.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably contain one or more compounds selected from group A and/or group B and/or group C. The proportions by weight of the compounds from these groups in the media according to the invention are preferably Group A: 0 to 90%, preferably 4 to 80%, in particular 4 to 50%

Group B: 0 to 80%, preferably 5 to 80%, in particular 5 to 65%

Group C: 0 to 80%, preferably 5 to 70%, in particular 5 to 50%, the sum of the proportions by weight of the group A and/or B and/or C compounds present in the particular media according to the invention preferably being 5 to 90% and in particular 10 to 80%.

The media according to the invention preferably contain 5 to 80%, particularly preferably 10 to 55%, of compounds according to the invention. Further preferred media are those which contain more than 60%, in particular 65 to 90%, of compounds according to the invention. The media preferably contain three, four or five compounds according to the invention.

Preferred embodiments of the liquid-crystalline media are indicated below:

In addition to one or more compounds of the formula I, the medium contains further compounds, preferably selected from the following group:

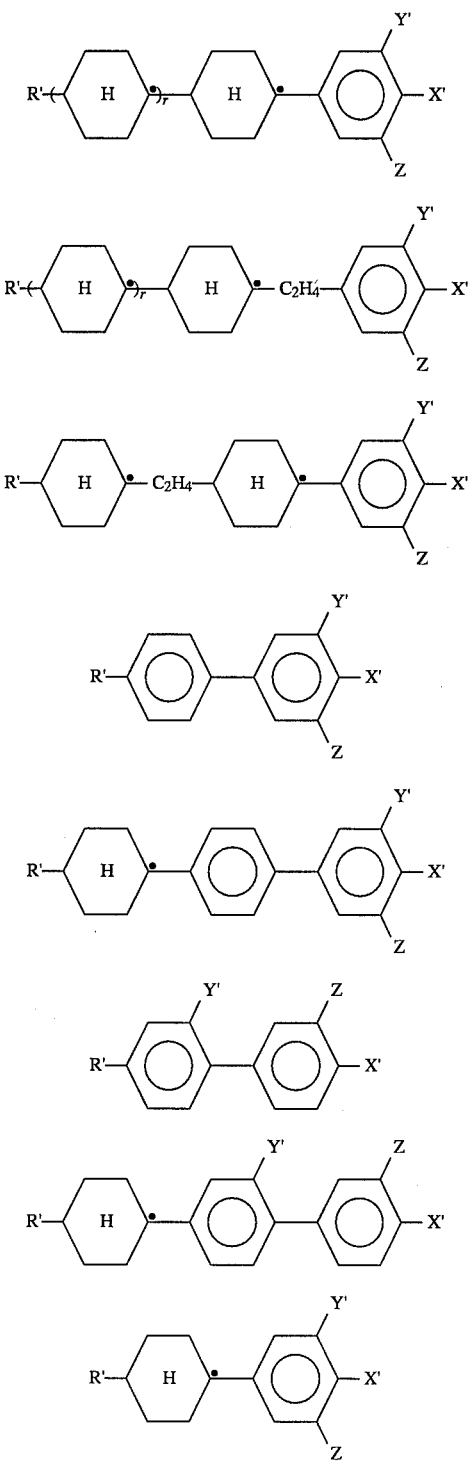

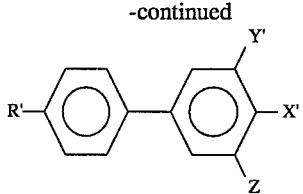

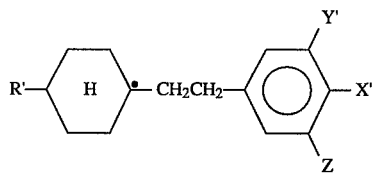

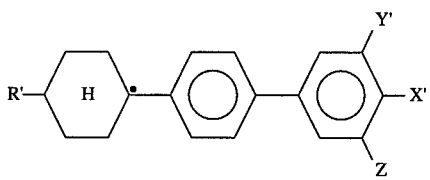

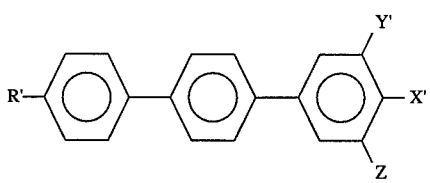

in which the individual radicals are defined as follows:

R': alkyl, oxaalkyl, fluoroalkyl or alkenyl, in each case having up to 7 carbon atoms, X': F, Cl, CF$_3$, OCF$_3$ or OCHF$_2$, Y' and Z: each, independently of the other, H or F, and r: 0 or 1.

In the formulae,

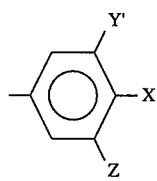

is preferably

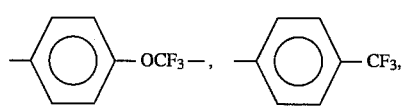

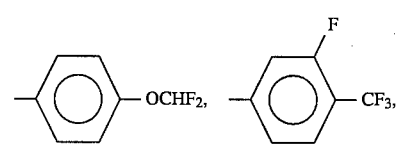

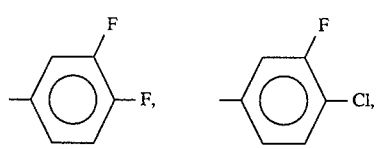

-continued

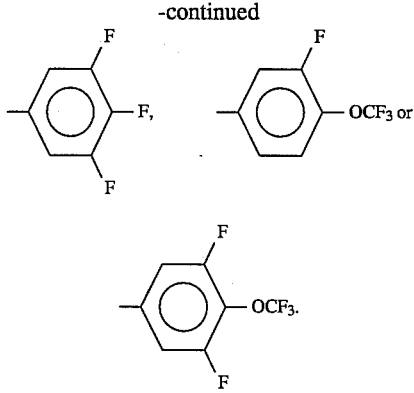

R' is preferably straight-chain alkyl having 1 to 7 carbon atoms

In addition to one or more compounds of the formula I, the medium preferably additionally contains one or more compounds selected from the group consisting of the general formulae II, III and IV. The proportion of compounds of the formulae II to IV in the total mixture is preferably from 30 to 70% by weight. Preference is furthermore given to media which are distinguished by the fact that they essentially comprise compounds of the general formulae I to XIII.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

In the present application and in the examples below, the structures of the liquid-crystal compounds are indicated by acronyms, with the transformation into chemical formulae being carried out in accordance with Tables A and B below. All radicals $C_nH_{2n+1}$ and $C_mH_{2m+1}$ are straight-chain alkyl radicals having n or m carbon atoms respectively. The coding in Table B is self-evident. In Table A, only the acronym for the parent structure is shown. In individual cases, the acronym for the parent structure is followed, separated by a dash, by a code for the substituents $R^1$, $R^2$, $L^1$ and $L^2$:

| Code for $R^1, R^2, L^1, L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_3$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |
| nAm | $C_nH_{2n+1}$ | $COOC_mH_{2m+1}$ | H | H |

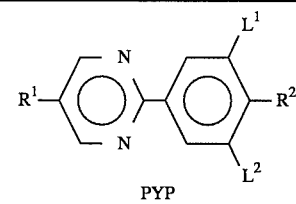

PYP

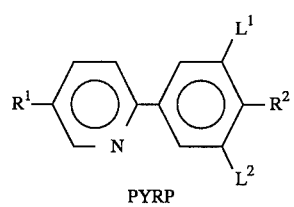

PYRP

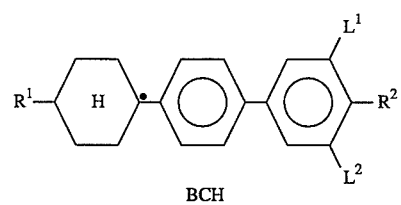

BCH

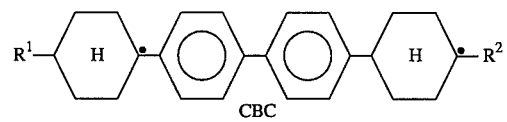

CBC

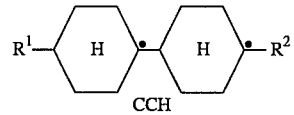

CCH

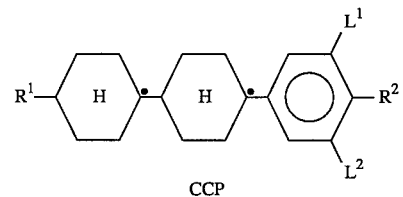

CCP

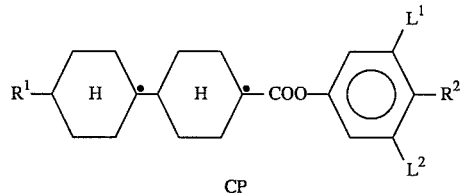

CP

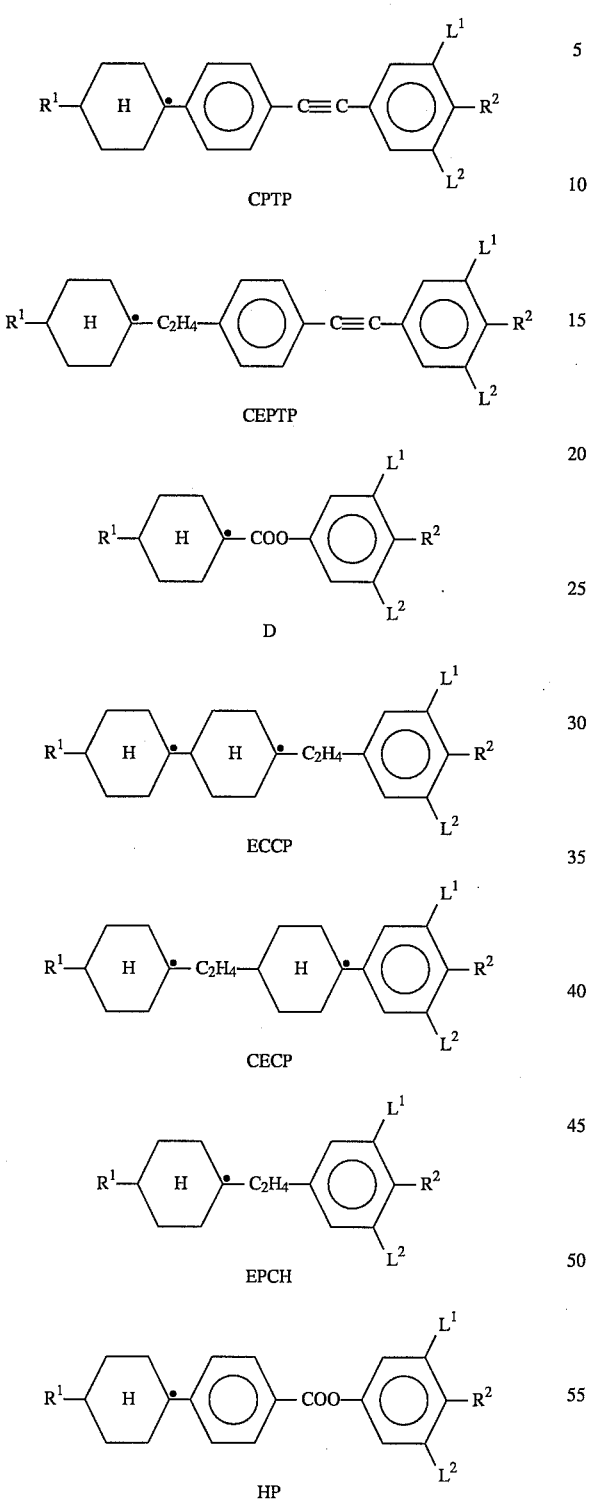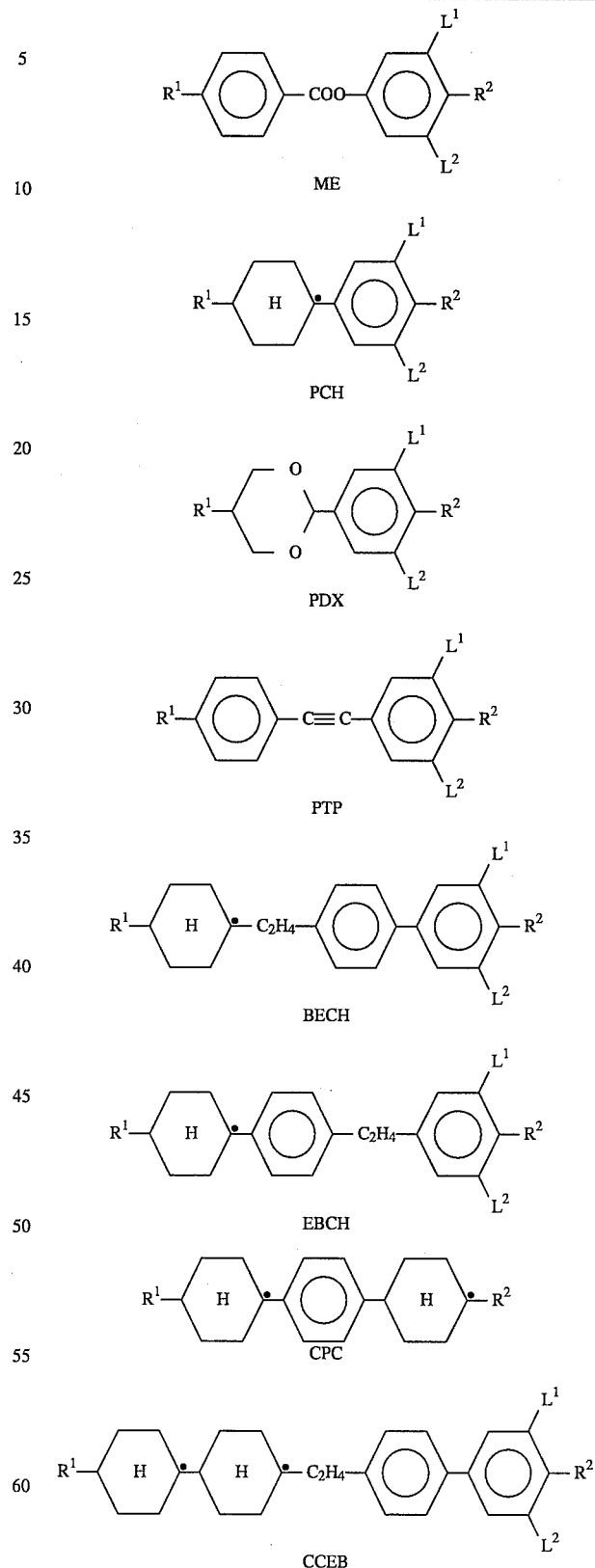

-continued

CCB: R¹—[H]—[H]—◯—◯(L¹,L²)—R²

CCB-n.FX: $C_nH_{2n+1}$—[H]—[H]—◯(F)—◯—X

B: R¹—◯—◯(L¹,L²)—R²

B-n.FX: $C_nH_{2n+1}$—◯(F)—◯—X

TABLE B

T15: $C_5H_{11}$—◯—◯—◯—CN

K3n: $C_nH_{2n+1}$—◯—◯—CN

M3n: $C_nH_{2n+1}$—O—◯—◯—CN

BCH-n.Fm: $C_nH_{2n+1}$—[H]—◯(F)—◯—$C_mH_{2m+1}$

C15: $C_2H_5$—CH(CH₃)—CH₂—O—◯—◯—CN (*)

CB15: $C_2H_5$—CH(CH₃)—CH₂—◯—◯—CN (*)

CBC-nmF: $C_nH_{2n+1}$—[H]—◯—◯(F)—[H]—$C_mH_{2m+1}$ $C_nH_{2n+1}$—◯—COO—◯—CN

TABLE B-continued

MEnN

ECBC-nm: $C_nH_{2n+1}$—[H]—$C_2H_4$—◯—◯—[H]—$C_mH_{2m+1}$

ECCH-nm: $C_nH_{2n+1}$—[H]—$C_2H_4$—[H]—$C_mH_{2m+1}$

CCP-nF.F.F: $C_nH_{2n+1}$—[H]—[H]—◯(F,F,F)

BCH-nF.F.F: $C_nH_{2n+1}$—[H]—◯—◯(F,F,F)

FET-nF(.F): $C_nH_{2n+1}$—◯(F)—◯—CH₂CH₂—◯(F,(F))—F

CFET-nF(.F): $C_nH_{2n+1}$—[H]—◯(F)—◯—CH₂CH₂—◯(F,(F))—F

CUP-nKCF₃.F.F: $C_nH_{2n+1}$—[H]—◯(F,F)—◯(F,F)—C(=O)—CF₃

CGP-nKCF₃.F.F: $C_nH_{2n+1}$—[H]—◯—◯(F,F)—C(=O)—CF₃

CCP-nKCF₃.F.F: $C_nH_{2n+1}$—[H]—[H]—◯(F,F)—C(=O)—CF₃

BCH-nKCF₃.F.F: $C_nH_{2n+1}$—[H]—◯—◯(F,F)—C(=O)—CF₃

The examples below are intended to illustrate the invention without representing a limitation. Above and below, per cent data are per cent by weight. All temperatures are given in degrees Celsius; mp.=melting point, cp.=clearing point. Furthermore, C=crystalline state, N=nematic phase, S=smectic phase and I=isotropic phase. The data between these symbols are the transition temperatures. An denotes optical anisotropy (589 nm, 20° C.), and the viscosity (mm²/sec) was determined at 20° C.

"Customary work-up" means that water is added, if necessary, the mixture is extracted with dichloromethane, diethyl ether or toluene, the organic phase is separated off, dried and evaporated, and the product is purified by distillation under reduced pressure or by crystallization and/or chromatography. The following abbreviations are used:

DAST diethylaminosulfur trifluoride
DCC dicyclohexylcarbodiimide
DDQ dichlorodicyanobenzoquinone
DIBALH diisobutylaluminium hydride
POT potassium tert-butoxide
THF tetrahydrofuran
pTSOH p-toluenesulphonic acid
TMEDA tetramethylethylenediamine Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 43 14 872.7, filed May 5, 1993, and German P 43 01 699.5, filed May 5, 1993, are hereby incorporated by reference.

EXAMPLE 1

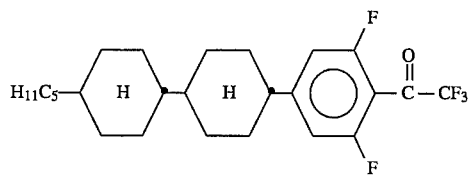

0.019 mol of p-[trans-4-(trans-4-pentylcyclohexyl)cyclohexyl]-2,6-difluorobenzene in 60 ml of absolute tetrahydrofuran are cooled to −70° C., and 0.023 mol of butyllithium (15% in n-hexane) is added. The mixture is stirred for 1.5 hours, and 0.02 mol of ethyl trifluoroacetate is subsequently added dropwise to the solution. The mixture is stirred at −70° C. for a further 2 hours, and finally about 6 ml of 12% hydrochloric acid are added. The organic phase is separated off, washed with water and subjected to customary work-up.

C 43 N 103.5 I, Δn=+0.091, Δε=17.45

The following compounds of the formula

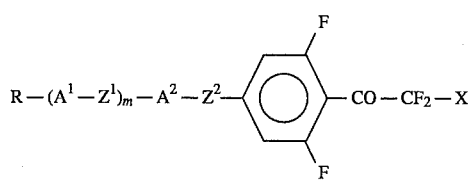

are prepared analogously:

| R | $-(A^1-Z^1)_m-A^2-Z^2-$ | X |
|---|---|---|
| n-C₃H₇ | —⟨H⟩— | F |
| n-C₃H₇ | —⟨H⟩— | Cl |
| n-C₅H₁₁ | —⟨H⟩— | F |
| n-C₅H₁₁ | —⟨H⟩— | Cl |
| n-C₃H₇ | —⟨O⟩— | F |
| n-C₃H₇ | —⟨O⟩— | Cl |
| n-C₅H₁₁ | —⟨O⟩— | F |
| n-C₅H₁₁ | —⟨O⟩— | Cl |
| CH₂=CHCH₂CH₂ | —⟨O⟩— | F |
| CH₃O | —⟨O⟩— | Cl |
| C₂H₅ | —⟨H⟩—⟨H⟩—CH₂CH₂— | F |
| n-C₃H₇ | —⟨H⟩—⟨H⟩—CH₂CH₂— | F |
| n-C₃H₇ | —⟨H⟩—⟨H⟩—CH₂CH₂— | Cl |
| n-C₅H₁₁ | —⟨H⟩—⟨H⟩—CH₂CH₂— | F |

-continued
| R | $-(A^1-Z^1)_m-A^2-Z^2-$ | X |
|---|---|---|
| n-C$_5$H$_{11}$ | 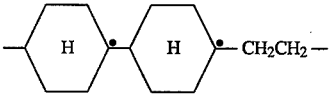 | Cl |
| CH$_3$OCH$_2$ | 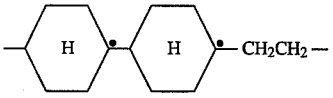 | F |
| C$_2$H$_5$ |  | F |
| C$_2$H$_5$ |  | Cl |
| n-C$_3$H$_7$ |  | F |
| n-C$_3$H$_7$ |  | Cl |
| n-C$_4$H$_9$ | 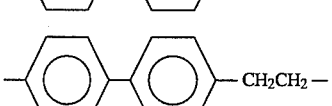 | F |
| n-C$_4$H$_9$ | 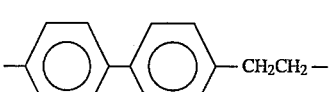 | Cl |
| n-C$_5$H$_{11}$ | 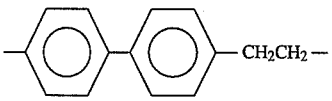 | F |
| n-C$_5$H$_{11}$ | 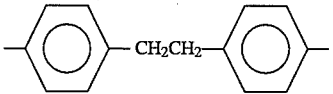 | Cl |
| C$_2$H$_5$ | 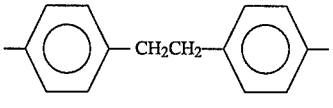 | F |
| C$_2$H$_5$ | 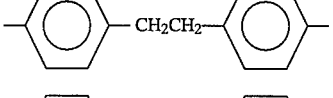 | Cl |
| n-C$_3$H$_7$ |  | F |
| n-C$_3$H$_7$ |  | Cl |
-continued
| R | $-(A^1-Z^1)_m-A^2-Z^2-$ | X |
|---|---|---|
| n-C$_5$H$_{11}$ | 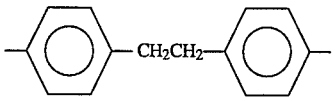 | F |
| n-C$_5$H$_{11}$ | 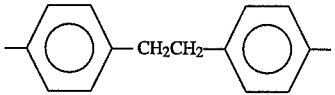 | Cl |
| CH$_2$=CHCH$_2$ | 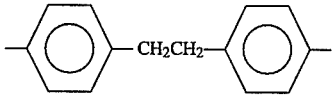 | F |
| CH$_2$=CHCH$_2$ | 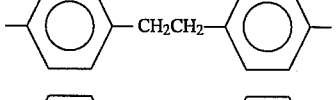 | Cl |
| n-C$_3$H$_7$ | 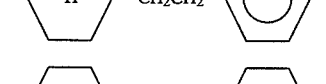 | F |
| n-C$_3$H$_7$ |  | Cl |
| n-C$_5$H$_{11}$ | 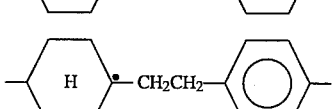 | F |
| n-C$_5$H$_{11}$ | 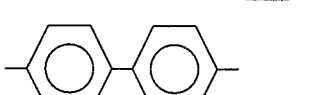 | Cl |
| n-C$_3$H$_7$ | 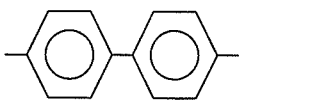 | F |
| n-C$_3$H$_7$ | 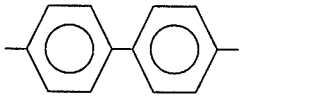 | Cl |
| n-C$_5$H$_{11}$ | 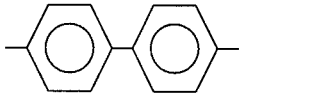 | F |
| n-C$_5$H$_{11}$ | 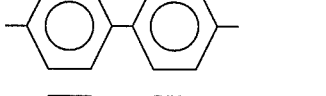 | Cl |
| CH$_3$CH$_2$O | | F |
| CH$_3$CH$_2$O | | Cl |

-continued

| R | $-(A^1-Z^1)_m-A^2-Z^2-$ | X |
|---|---|---|
| $C_2H_5$ | Cy-Cy | F |
| n-$C_3H_7$ | Cy-Cy | F C78N94.8 I;Δn =+0.097;Δε =18.21 |
| n-$C_3H_7$ | Cy-Cy | Cl |
| n-$C_4H_9$ | Cy-Cy | F |
| n-$C_4H_9$ | Cy-Cy | Cl |
| n-$C_5H_{11}$ | Cy-Cy | Cl |
| n-$C_6H_{13}$ | Cy-Cy | F |
| n-$C_6H_{13}$ | Cy-Cy | Cl |
| n-$C_{10}H_{21}$ | Cy-Cy | F |
| n-$C_{12}H_{25}$ | Cy-Cy | F |
| n-$C_3H_7$ | Cy-Ph(3-F) | F |
| n-$C_3H_7$ | Cy-Ph(3-F) | Cl |
| n-$C_4H_9$ | Cy-Ph(3-F) | F |

-continued

| R | $-(A^1-Z^1)_m-A^2-Z^2-$ | X |
|---|---|---|
| n-$C_4H_9$ | Cy-Ph(3-F) | Cl |
| n-$C_5H_{11}$ | Cy-Ph(3-F) | F |
| n-$C_5H_{11}$ | Cy-Ph(3-F) | Cl |
| n-$C_3H_7$ | Cy-Ph(3,5-F) | F |
| n-$C_3H_7$ | Cy-Ph(3,5-F) | Cl |
| n-$C_5H_{11}$ | Cy-Ph(3,5-F) | F |
| n-$C_5H_{11}$ | Cy-Ph(3,5-F) | Cl |
| n-$C_3H_7$ | Cy-Ph(3,5-F)-$CH_2CH_2-$ | F |

| R | $-(A^1-Z^1)_m-A^2-Z^2-$ | X |
|---|---|---|
| n-C₃H₇ | 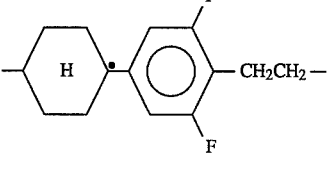 | Cl |
| n-C₅H₁₁ | 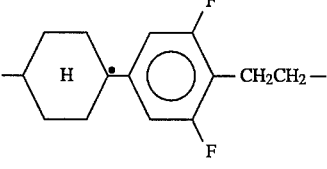 | F |
| n-C₅H₁₁ | 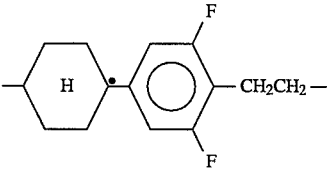 | Cl |
| C₂H₅ | 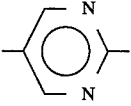 | F |
| C₂H₅ | 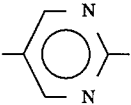 | Cl |
| n-C₃H₇ | 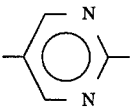 | F |
| n-C₃H₇ | 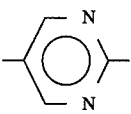 | Cl |
| n-C₅H₁₁ | 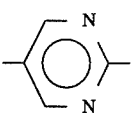 | F |
| n-C₅H₁₁ | 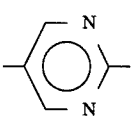 | Cl |
| C₂H₅ | 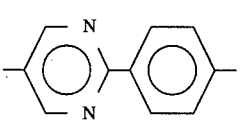 | F |
| C₂H₅ | 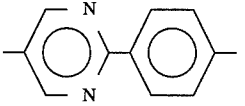 | Cl |
| n-C₃H₇ | 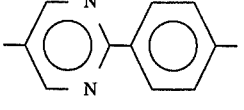 | F |
| n-C₃H₇ | 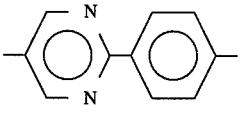 | Cl |
| n-C₅H₁₁ | 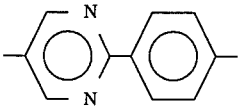 | F |
| n-C₅H₁₁ | 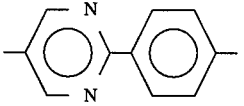 | Cl |
| C₂H₅ | 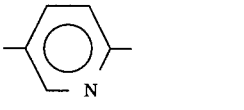 | F |
| C₂H₅ | 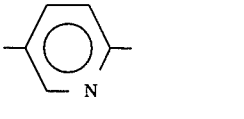 | Cl |
| n-C₃H₇ | 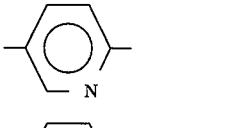 | F |
| n-C₃H₇ | 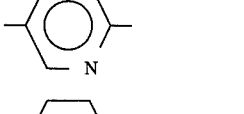 | Cl |
| n-C₅H₁₁ | 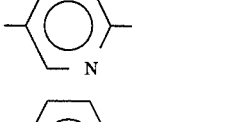 | F |
| n-C₅H₁₁ |  | Cl |
| C₂H₅ | 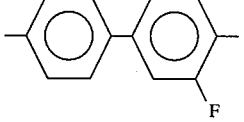 | F |

-continued

| R | $-(A^1-Z^1)_m-A^2-Z^2-$ | X |
|---|---|---|
| $C_2H_5$ | phenyl–(3,5-difluoro)phenyl– | Cl |
| n-$C_3H_7$ | phenyl–(3,5-difluoro)phenyl– | F |
| n-$C_3H_7$ | phenyl–(3,5-difluoro)phenyl– | Cl |
| n-$C_5H_{11}$ | phenyl–(3,5-difluoro)phenyl– | F |
| n-$C_3H_7$ | phenyl–(3,5-difluoro)phenyl– | Cl |
| $C_2H_5$ | trans-cyclohexyl–CH$_2$CH$_2$– | F |
| $C_2H_5$ | trans-cyclohexyl–CH$_2$CH$_2$– | Cl |
| n-$C_3H_7$ | trans-cyclohexyl–CH$_2$CH$_2$– | F |
| n-$C_3H_7$ | trans-cyclohexyl–CH$_2$CH$_2$– | Cl |
| n-$C_5H_{11}$ | trans-cyclohexyl–CH$_2$CH$_2$– | F |
| n-$C_5H_{11}$ | trans-cyclohexyl–CH$_2$CH$_2$– | Cl |

-continued

| R | $-(A^1-Z^1)_m-A^2-Z^2-$ | X |
|---|---|---|
| $C_2H_5$ | 1,3-dioxane | F |
| $C_2H_5$ | 1,3-dioxane | Cl |
| n-$C_3H_7$ | 1,3-dioxane | F |
| n-$C_3H_7$ | 1,3-dioxane | Cl |
| n-$C_5H_{11}$ | 1,3-dioxane | F |
| n-$C_5H_{11}$ | 1,3-dioxane | Cl |
| $C_2H_5$ | phenyl–(3-fluoro)phenyl– | F |
| $C_2H_5$ | phenyl–(3-fluoro)phenyl– | Cl |
| n-$C_3H_7$ | phenyl–(3-fluoro)phenyl– | F |
| n-$C_3H_7$ | phenyl–(3-fluoro)phenyl– | Cl |
| n-$C_5H_{11}$ | phenyl–(3-fluoro)phenyl– | F |

-continued

| R | $-(A^1-Z^1)_m-A^2-Z^2-$ | X |
|---|---|---|
| n-C$_5$H$_{11}$ | 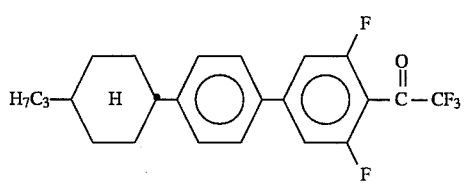 | Cl |

EXAMPLE 2

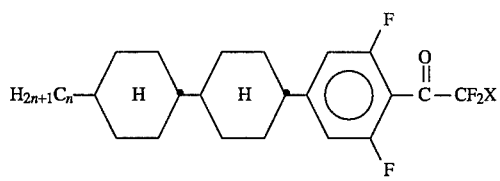

0.03 mol of p-[4-(trans-4-propylcyclohexyl)-phenyl]-2,6-difluorobenzene in 60 ml of absolute tetrahydrofuran is cooled to −70° C., and 0.034 mol of butyl-lithium (15% in n-hexane) is subsequently added. The mixture is stirred at −70° C. for 2 hours, and 0.031 mol of ethyl trifluoroacetate is added dropwise. The mixture is stirred for a further 2 hours, 5 ml of 12.5% hydrochloric acid are added, and the organic phase is separated off and then subjected to customary work-up.

C 57N (49.5) I, Δn=+0.164

The following compounds of the formula $$H_{2n+1}C_n-\boxed{H}-\boxed{H}-\boxed{\phantom{}}-\underset{F}{\overset{F}{\phantom{}}}C(=O)-CF_2X$$

are prepared analogously:

| n | X |
|---|---|
| 1 | F |
| 1 | Cl |
| 1 | H |
| 2 | F |
| 2 | Cl |
| 2 | H |
| 3 | Cl |
| 3 | H |
| 4 | F |
| 4 | Cl |
| 4 | H |

-continued

| n | X |
|---|---|
| 5 | Cl |
| 5 | H |
| 6 | F |
| 6 | Cl |
| 6 | H |
| 8 | F |
| 8 | Cl |
| 8 | H |
| 10 | F |
| 10 | Cl |
| 10 | H |

EXAMPLE 3

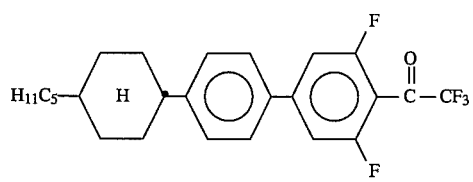

2.0 mol of NaOH pellets are dissolved in 500 ml of water, and 0.5 mol of p-[trans-4-pentylcyclohexyl]-phenylboronic acid in 1000 ml of toluene is added. The mixture is subsequently stirred for 40 minutes, during which the temperature of the solution should not exceed 45° C. 0.5 mol of 3,5-difluorophenyl bromide and 11.5 g of tetrakis(triphenylphosphine)palladium(0) are then added to the solution. The mixture is refluxed overnight and cooled to room temperature.

The mixture is filtered with suction, the organic phase is separated off, and the aqueous phase is extracted with toluene. The combined organic extracts are washed with water and filtered through a spherical frit filled with silica gel. The solution is subsequently dried over NaSO$_4$. The solvent is removed in vacuo, and the residue is recrystallized from ethanol.

The product (0.03 mol) is dissolved in THF at room temperature with stirring under a nitrogen atmosphere. The solution is then cooled to −70° C., and 0.034 mol of n-BuLi (15% in n-hexane) is added dropwise. The mixture is stirred at −70° C. for 2 hours, 0.031 mol of ethyl trifluoroacetate is added dropwise to the suspension, and the mixture is stirred for a further 2 hours. 12.5% hydrochloric acid is subsequently added. Finally, the mixture is subjected to conventional work-up.

Cl. pt. 70.5° C., Δε=22, Δn=0.155

Mixture Examples

| Example A | | | |
|---|---|---|---|
| PCH-5F | 5.0 | Clearing point [°C.]: | +88 |
| PCH-7F | 6.0 | Δn 589 nm, 20 [°C.]: | +0.0913 |
| CCP-2OCF$_3$ | 11.0 | Δε [1 kHz, 20° C.]: | 8.6 |
| CCP-3OCF$_3$ | 12.0 | V$_{(10,0,20)}$ [V]: | 1.49 |

-continued

| | | | |
|---|---|---|---|
| CCP-4OCF$_3$ | 10.0 | V$_{(90,0,20)}$ [V]: | 2.34 |
| CCP-5OCF$_3$ | 12.0 | | |
| BCH-3F.F.F | 12.0 | | |
| BCH-5F.F.F | 11.0 | | |
| CCP-3F.F.F | 12.0 | | |
| CCP-5KCF$_3$.F.F | 9.0 | | |

Example B

| | | | |
|---|---|---|---|
| OCH-5F | 5.0 | Clearing point [°C.]: | +88 |
| PCH-7F | 6.0 | Δn [589 nm, 20° C.]: | +0.0969 |
| CCP-2OCF$_3$ | 11.0 | Δε [1 kHz, 20° C.]: | 9.2 |
| CCP-3OCF$_3$ | 12.0 | V$_{(10,0,20)}$ [V]: | 1.31 |
| CCP-4OCF$_3$ | 10.0 | V$_{(90,0,20)}$ [V]: | 2.10 |
| CCP-5OCF$_3$ | 12.0 | | |
| BCH-3KCF$_3$.F.F | 12.0 | | |
| BCH-5F.F.F | 11.0 | | |
| CCP-3F.F.F | 12.0 | | |
| CCP-5F.F.F | 9.0 | | |

Example C

| | | | |
|---|---|---|---|
| PCH-5F | 5.0% | Clearing point [°C.]: | +87 |
| PCH-7F | 6.0% | Δn [589 nm, 20° C.]: | +0.0978 |
| CCP-2OCF$_3$ | 11.0% | V$_{(10,0,20)}$ [V]: | 1.50 |
| CCP-3OCF$_3$ | 12.0% | V$_{(90,0,20)}$ [V]: | 2.30 |
| CCP-4OCF$_3$ | 10.0% | | |
| CCP-5OCF$_3$ | 12.0% | | |
| BCH-3F.F.F | 12.0% | | |
| BCH-5F.F.F | 11.0% | | |
| CCP-5KCF$_3$.F.F | 21.0% | | |

Example D

| | | | |
|---|---|---|---|
| PCH-5F | 5.0% | Clearing point [°C.]: | +87 |
| PCH-7F | 6.0% | Δn [589 nm, 20° C.]: | +0.1008 |
| CCP-2OCF$_3$ | 11.0% | V$_{(10,0,20)}$ [V]: | 1.31 |
| CCP-3OCF$_3$ | 12.0% | V$_{(90,0,20)}$ [V]: | 2.05 |
| CCP-4OCF$_3$ | 10.0% | | |
| CCP-5OCF$_3$ | 12.0% | | |
| BCH-3KCF$_3$.F.F | 23.0% | | |
| CCP-3F.F.F | 12.0% | | |
| CCP-5F.F.F | 9.0% | | |

Example E

| | | | |
|---|---|---|---|
| PCH-5F | 5.0% | Clearing point [°C.]: | +87 |
| PCH-7F | 6.0% | Δn [589 nm, 20° C.]: | +0.1052 |
| CCP-2OCF$_3$ | 11.0% | V$_{(10,0,20)}$ [V]: | 1.26 |
| CCP-3OCF$_3$ | 12.0% | V$_{(90,0,20)}$ [V]: | 1.99 |
| CCP-4OCF$_3$ | 10.0% | | |
| CCP-5OCF$_3$ | 12.0% | | |
| BCH-3KCF$_3$.F.F | 23.0% | | |
| CCP-5KCF$_3$.F.F | 21.0% | | |

Example F

| | | | |
|---|---|---|---|
| PCH-5F | 9.0% | Clearing point [°C.]: | 90.0 |
| PCH-6F | 7.2% | Δn [589 nm, 20° C.]: | 0.1015 |
| PCH-7F | 5.4% | Δε [1 kHz, 20° C.]: | 6.57 |
| CCP-2OCF$_3$ | 7.2% | | |
| CCP-3OCF$_3$ | 10.8% | | |
| CCP-4OCF$_3$ | 8.1% | | |
| CCP-5OCF$_3$ | 8.1% | | |
| BCH-3F.F | 10.8% | | |
| BCH-5F.F | 9.0% | | |
| ECCP-3OCF$_3$ | 4.5% | | |
| ECCP-5OCF$_3$ | 4.5% | | |
| CBC-33F | 1.8% | | |
| CBC-53F | 1.8% | | |
| CBC-55F | 1.8% | | |
| CCP-3KCF$_3$.F.F | 10.0% | | |

Example G

| | | | |
|---|---|---|---|
| PCH-5F | 9.0% | Clearing point [°C.]: | 91.1 |
| PCH-6F | 7.2% | Δn [589 nm, 20° C.]: | 0.0964 |
| PCH-7F | 5.4% | Δε [1 kHz, 20° C.]: | 6.46 |
| CCP-2OCF$_3$ | 7.2% | | |
| CCP-3OCF$_3$ | 10.8% | | |
| CCP-4OCF$_3$ | 8.1% | | |
| CCP-5OCF$_3$ | 8.1% | | |
| BCH-3F.F | 10.8% | | |
| BCH-5F.F | 9.0% | | |
| ECCP-3OCF$_3$ | 4.5% | | |

-continued

| | | | |
|---|---|---|---|
| ECCP-5OCF$_3$ | 4.5% | | |
| CBC-33F | 1.8% | | |
| CBC-53F | 1.8% | | |
| CBC-55F | 1.8% | | |
| CCP-5KCF$_3$.F.F | 10.0% | | |

Example H

| | | | |
|---|---|---|---|
| PCH-5F | 9.0% | Clearing point [°C.]: | 88.9 |
| PCH-6F | 7.2% | Δn [589 nm, 20° C.]: | 0.1037 |
| PCH-7F | 5.4% | Δε [1 kHz, 20° C.]: | 7.17 |
| CCP-2OCF$_3$ | 7.2% | | |
| CCP-3OCF$_3$ | 10.8% | | |
| CCP-4OCF$_3$ | 8.1% | | |
| CCP-5OCF$_3$ | 8.1% | | |
| BCH-3F.F | 10.8% | | |
| BCH-5F.F | 9.0% | | |
| ECCP-3OCF$_3$ | 4.5% | | |
| ECCP-5OCF$_3$ | 4.5% | | |
| CBC-33F | 1.8% | | |
| CBC-53F | 1.8% | | |
| CBC-55F | 1.8% | | |
| CCP-3KCF$_3$.F.F | 10.0% | | |

Example I

| | | | |
|---|---|---|---|
| PCH-2 | 5.0% | Clearing point [°C.]: | 61 |
| PCH-3 | 15.0% | Δn [589 nm, 20° C.]: | 0.1270 |
| PCH-4 | 11.0% | Δε [1 kHz, 20° C.]: | 16.6 |
| PCH-5 | 21.0% | d.Δn [μm]: | 1.0 |
| PCH-7 | 11.0% | $V_{(10,0,20)}$ [V]: | 1.53 |
| PCH-32 | 5.0% | $V_{(90,0,20)}$ [V]: | 2.09 |
| BCH-3KCF$_3$.F.F | 12.0% | | |
| BCH-5KCF$_3$.F.F | 10.0% | | |
| CBC-33 | 4.0% | | |
| CBC-53 | 6.0% | | |

Example J

| | | | |
|---|---|---|---|
| PCH-3 | 14.0% | Clearing point [°C.]: | 87 |
| PCH-4 | 10.0% | Δn [589 nm, 20° C.]: | 0.1320 |
| PCH-5 | 20.0% | Δε [1 kHz, 20° C.]: | 15.1 |
| PCH-7 | 10.0% | d.Δn [μm]: | 1.0 |
| PCH-32 | 5.0% | $V_{(10,0,20)}$ [V]: | 1.61 |
| BCH-3KCF$_3$.F.F | 12.0% | $V_{(10,0,20)}$ [V]: | 2.23 |
| BCH-5KCF$_3$.F.F | 10.0% | | |
| CBC-33 | 6.0% | | |
| CBC-53 | 7.0% | | |
| CBC-55 | 6.0% | | |

Example K

| | | | |
|---|---|---|---|
| PCH-3 | 12.0% | Clearing point [°C.]: | 86 |
| PCH-4 | 10.0% | Δn [589 nm, 20° C.]: | 0.1321 |
| PCH-5 | 18.0% | Δε [1 kHz, 20° C.]: | 16.5 |
| PCH-7 | 9.0% | d.Δn [μm]: | 1.0 |
| BCH-3KCF$_3$.F.F | 9.0% | $V_{(10,0,20)}$ [V]: | 1.52 |
| BCH-5KCF$_3$.F.F | 9.0% | $V_{(90,0,20)}$ [V]: | 2.14 |
| CCP-3KCF$_3$.F.F | 9.0% | | |
| CCP-5KCF$_3$.F.F | 9.0% | | |
| CBC-33 | 4.0% | | |
| CBC-53 | 5.0% | | |
| CBC-55 | 6.0% | | |

Example L

| | | | |
|---|---|---|---|
| PCH-3 | 14.0% | Clearing point [°C.]: | 90° C. |
| PCH-4 | 10.0% | Δn [589 nm, 20° C.]: | 0.118 |
| PCH-5 | 20.0% | Δε [1 kHz, 20° C.]: | 13.7 |
| PCH-7 | 10.0% | d.Δn [μm]: | 1.0/0.5 |
| PCH-32 | 5.0% | $V_{(10,0,20)}$ [V]: | 1.67/1.32 |
| BCH-3KCF$_3$.F.F | 12.0% | $V_{(90,0,20)}$ [V]: | 2.38/2.07 |
| BCH-5KCF$_3$.F.F | 9.0% | | |
| CBC-33 | 6.0% | | |
| CBC-53 | 7.0% | | |
| CBC-55 | 6.0% | | |

Example M

| | | | |
|---|---|---|---|
| PCH-2 | 12.0% | Clearing point [°C.]: | 62 |
| PCH-4 | 13.0% | Δn [589 nm, 20° C.]: | +0.1385 |
| K6 | 7.0% | Δε [1 kHz, 20° C.]: | 17.3 |
| K9 | 6.0% | d.Δn [μm]: | 1.0 |
| K12 | 6.0% | $V_{(10,0,20)}$ [V]: | 1.17 |
| ME2N | 2.0% | $V_{(90,0,20)}$ [V]: | 1.76 |

-continued

| | | | |
|---|---|---|---|
| ME3N | 3.0% | | |
| ME2N.F | 3.0% | | |
| ME3N.F | 3.0% | | |
| ME5N.F | 5.0% | | |
| BCH-3KCF$_3$.F.F | 8.0% | | |
| BCH-5KCF$_3$.F.F | 8.0% | | |
| HD-34 | 6.0% | | |
| HD-35 | 7.0% | | |
| CH-33 | 3.0% | | |
| CH-35 | 3.0% | | |
| CH-43 | 3.0% | | |
| CH-45 | 3.0% | | |
| Example N | | | |
| PCH-3 | 7.0% | Clearing point [°C.]: | 71 |
| PCH-4 | 4.0% | Δn [589 nm, 20° C.]: | +0.1430 |
| K6 | 12.0% | Δε [1 kHz, 20° C.]: | 11.1 |
| K12 | 12.0% | d.Δn [µm]: | 1.0 |
| PCH-301 | 4.0% | V$_{(10,0,20)}$ [V] | 1.45 |
| BCH-3KCF$_3$.F.F | 8.0% | V$_{(90,0,20)}$ [V] | 2.60 |
| BCH-5KCF$_3$.F.F | 7.0% | | |
| D-301 | 8.0% | | |
| D-302 | 7.0% | | |
| D-401 | 6.0% | | |
| D-402 | 6.0% | | |
| D-501 | 7.0% | | |
| CBC-33 | 4.0% | | |
| CBC-53 | 4.0% | | |
| CBC-55 | 4.0% | | |
| Example O | | | |
| ME2N.F | 3.0% | Clearing point [°C.]: | 81 |
| ME3N.F | 3.0% | Δn [589 nm, 20° C.]: | +0.1580 |
| ME5N.F | 6.0% | Δε [1 kHz, 20° C.]: | 17.4 |
| ME7N.F | 5.0% | | |
| HP-3N.F | 5.0% | Twist angle: | 180° (STN) |
| K9 | 6.0% | V$_{(10,0,20)}$ [V]: | 1.26 |
| K15 | 12.0% | | |
| PCH-3 | 14.0% | V$_{90}$/V$_{10}$: | 15.7 |
| PCH-301 | 18.0% | | |
| BCH-3KCF$_3$.F.F | 6.0% | | |
| CBC-33 | 5.0% | | |
| CBC-55 | 4.0% | | |
| CBC-33F | 4.0% | | |
| CBC-53F | 5.0% | | |
| CBC-55F | 4.0% | | |
| Example P | | | |
| PCH-3 | 9.5% | Clearing point [°C.]: | 88 |
| PCH-4 | 6.5% | Δn [589 nm, 20° C.]: | +0.1388 |
| PCH-5 | 13.0% | Δε [1 kHz, 20° C.]: | +15.3 |
| PCH-7 | 6.5% | d.Δn [µm]: | 1.0 |
| PCH-302 | 12.5% | V$_{(10,0,20)}$ [V]: | 1.65 |
| BCH-3KCF$_3$.F.F | 18.0% | V$_{(90,0,20)}$ [V]: | 2.30 |
| BCH-5KCF$_3$.F.F | 18.0% | | |
| CBC-33 | 5.0% | | |
| CBC-53 | 5.0% | | |
| CBC-55 | 6.0% | | |
| Example Q | | | |
| Multi-bottle system | | | |
| -000 | | -050 | |
| PCH-3 | 12.0% | PCH-3 | 11.0% |
| PCH-4 | 9.0% | PCH-4 | 8.0% |
| PCH-5 | 18.0% | PCH-5 | 16.0% |
| PCH-7 | 9.0% | PCH-7 | 8.0% |
| BCH-3KCF$_3$.F.F | 3.0% | PCH-302 | 5.0% |
| BCH-5KCF$_3$.F.F | 3.0% | BCH-3KCF$_3$.F.F | 9.0% |
| CCP-3KCF$_3$.F.F | 15.0% | BCH-5KCF$_3$.F.F | 9.0% |
| CCP-5KCF$_3$.F.F | 15.0% | CCP-3KCF$_3$.F.F | 9.0% |
| CBC-33 | 5.0% | CCP-5KCF$_3$.F.F | 9.0% |
| CBC-53 | 5.0% | CBC-33 | 5.0% |
| CBC-55 | 6.0% | CBC-53 | 5.0% |
| | | CBC-55 | 6.0% |
| Clearing point: | 87 | Clearing point [°C.]: | 87 |
| Δn [589 nm, 20° C.]: | +0.122 | Δn [589 nm, 20° C.]: | +0.135 |
| Δε [1 kHz, 20° C.]: | 15.7 | Δε [1 kHz, 20° C.]: | 15.5 |
| d.Δn [µm]: | 1.0 | d.Δn [µm]: | 1.0 |
| V$_{(10,0,20)}$ [V]: | 1.60 | V$_{(10,0,20)}$ [V]: | 1.58 |

-continued

| | | | |
|---|---|---|---|
| $V_{(90,0,20)}$ [V] | 2.35 | $V_{(90,0,20)}$ [V]: | 2.29 |
| -100 | | | |
| PCH-3 | 10.0% | Clearing point [°C.]: | 88 |
| PCH-4 | 7.0% | $\Delta\epsilon$ [1 kHz, 20° C.]: | +15.4 |
| PCH-5 | 14.0% | d.$\Delta$n [µm]: | 1.0 |
| PCH-7 | 7.0% | $V_{(10,0,20)}$ [V]: | 1.58 |
| PCH-302 | 10.0% | $V_{(90,0,20)}$ [V]: | 2.24 |
| BCH-3KCF$_3$.F.F | 15.0% | | |
| BCH-5KCF$_3$.F.F | 15.0% | | |
| CCP-3KCF$_3$.F.F | 3.0% | | |
| CCP-5KCF$_3$.F.F | 3.0% | | |
| CBC-33 | 5.0% | | |
| CBC-53 | 5.0% | | |
| CBC-55 | 6.0% | | |

Example R

| | | | |
|---|---|---|---|
| PCH-3 | 20.0% | Clearing point [°C.]: | 73 |
| PCH-4 | 9.0% | $\Delta$n [589 nm, 20° C.]: | +0.1032 |
| PCH-5 | 9.0% | $\Delta\epsilon$ [1 kHz, 20° C.]: | 11.8 |
| PCH-301 | 15.0% | d,$\Delta$n [µm]: | 0.5 |
| CCP-2OCF$_3$ | 6.0% | Twist angle: | 240° (STN) |
| CCP-3OCF$_3$ | 6.0% | $V_{(10,0,20)}$ [V]: | 2.02 |
| CCP-5OCF$_3$ | 6.0 | $V_{90}/V_{10}$: | 6.5% |
| CCP-3KCF$_3$.F.F | 10.0% | | |
| CCP-5KCF$_3$.F.F | 10.0 | | |
| CBC-33F | 4.0% | | |
| CBC-53F | 5.0% | | |

Example S

Two-bottle System (STN)

| | | | | |
|---|---|---|---|---|
| -000 | | | -100 | |
| PCH-3 | 20.0% | | PCH-3 | 17.0% |
| PCH-4 | 9.0% | | K6 | 6.0% |
| | | | K9 | 7.0% |
| PCH-5 | 9.0% | | PCH-301 | 20.0% |
| PCH-301 | 15.0% | | PTP-102 | 6.0% |
| CCP-2OCF$_3$ | 6.0% | | PTP-201 | 6.0% |
| CCP-3OCF$_3$ | 6.0% | | CCP-3OCF$_3$ | 6.0% |
| CCP-5OCF$_3$ | 6.0% | | CCP-5OCF$_3$ | 6.0% |
| CCP-3KCF$_3$.F.F | 10.0% | | BCH-3KCF$_3$.F.F | 5.0% |
| CCP-5KCF$_3$.F.F | 10.0% | | BCH-5KCF$_3$.F.F | 5.0% |
| CCPC-33 | 3.0% | | CPTP-301 | 5.0% |
| CCPC-34 | 3.0% | | CPTP-302 | 6.0% |
| CCPC-35 | 3.0% | | CPTP-303 | 5.0% |
| Clearing point [°C.]: | 76 | | Clearing point [°C.]: | 82 |
| $\Delta$n [589 nm, 20° C.]: | +0.0966 | | $\Delta\epsilon$ [589 nm, 20° C.]: | +0.1785 |
| $\Delta\epsilon$ [1 kHz, 20° C.]: | 11.7 | | $\Delta\epsilon$ [1 kHz, 20° C.]: | 17.0 |
| d,$\Delta$n [µm]: | 0.5 | | d.$\Delta$n [µm]: | 0.5 |
| | TN | STN (240) | TN (90°) | STN (240°) |
| $V_{(10,0,20)}$ [V]: | 1.29 | 2.03 | $V_{(10,0,20)}$ [V]: 1.78 | 1.98 |
| $V_{(90,0,20)}$ [V]: | 2.08 | — | $V_{(90,0,20)}$ [V]: 2.50 | — |
| $V_{90}/V_{10}$: | — | 6.7% | $V_{90}/V_{10}$: — | 6.5% |

Example T

| | | | |
|---|---|---|---|
| PCH-3 | 17.0% | Clearing point [°C.]: | 81 |
| K6 | 6.0% | $\Delta$n [589 nm, 20° C.]: | +0.1823 |
| K9 | 7.0% | $\Delta\epsilon$ [1 kHz, 20° C.]: | 11.5 |
| PCH-301 | 18.0% | d.$\Delta$n [µm]: | 1.0 |
| PTP-102 | 6.0% | | |
| PTP-201 | 6.0% | TN (90°) | STN (240°) |
| CCP-3KCF$_3$.F.F | 6.0% | $V_{(10,0,20)}$ [V]: 1.66 | 1.90 |
| CCP-5KCF$_3$.F.F | 6.0% | $V_{(90,0,20)}$ [V]: 2.34 | — |
| BCH-3KCF$_3$.F.F | 5.0% | $V_{90}/V_{10}$: — | 6.8% |
| BCH-5KCF$_3$.F.F | 5.0% | | |
| CPTP-301 | 6.0% | | |
| CPTP-302 | 6.0% | | |
| CPTP-303 | 6.0% | | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Fluoromethyl ketones of the formula I

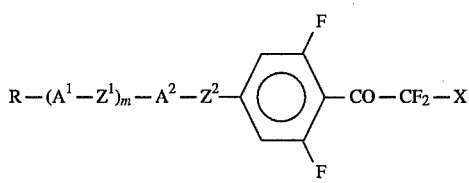

in which

R is H, an alkyl or alkenyl radical having 1 to 15 carbon atoms which is unsubstituted, monosubstituted by CN or $CF_3$ or substituted by halogen, and one or more $CH_2$ groups in these radicals is optionally replaced, in each case independently of one another, by —O—, —S—,

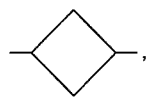

—CO—, —CO—O—, —O—CO— or —O—CO—O—, in such a way that O atoms are not linked directly to one another, $A^1$ and $A^2$ are each, independently of one another,
 (a) trans-1,4-cyclohexylene radical in which, in addition, one or more non-adjacent $CH_2$ groups is optionally replaced by —O— and/or —S—,
 (b) 1,4-phenylene radical in which, in addition, one or two CH groups is optionally replaced by N, or
 (c) radical from the group consisting of 1,4-cyclohexenylene, 1,4-bicyclo(2,2,2)octylene, piperidine-1,4-diyl, naphthalene-2,6-diyl, decahydronaphthalene-2,6-diyl and 1,2,3,4-tetrahydronaphthalene-2,6-diyl, wherein radicals (a) and (b) are optionally substituted by one or two fluorine atoms, $Z^1$ and $Z^2$ are each, independently of one another, —CO—O—, —O—CO—, —CHO—, —$OCH_2$—, —$CH_2CH_2$—, —CH=CH—, —C≡C— or a single bond, and one of the radicals $Z^1$ and $Z^2$ is optionally —$(CH_2)_4$— or —CH=CH—$CH_2CH_2$—, X is H, F or Cl and m is 0, 1 or 2.

2. Compounds of the formula I1,

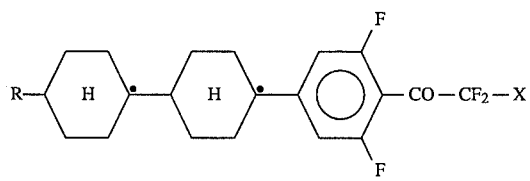

in which R and X are as defined in claim 1.

3. Compounds of the formula I3,

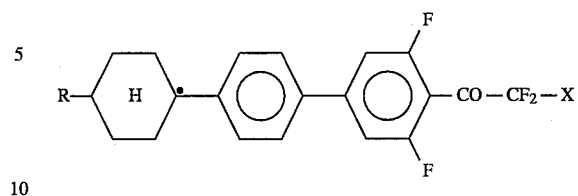

in which R and X are as defined in claim 1.

4. Compounds of the formula I4,

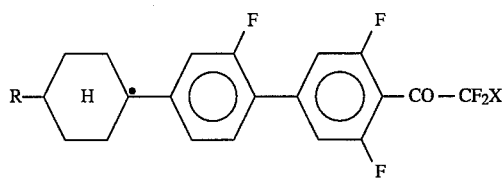

in which R and X are as defined in claim 1.

5. Compounds of the formula I5,

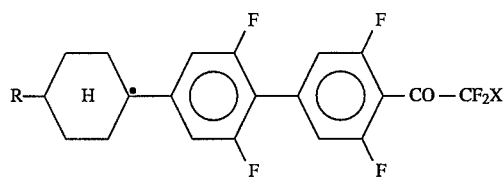

in which R and X are as defined in claim 1.

6. Compounds according to claim 1, wherein X is fluorine.

7. A method of using compounds of claim 1 as components of liquid-crystalline media which comprises adding said compounds to a liquid-crystalline medium.

8. Liquid-crystalline medium having at least two liquid-crystalline components, which contains at least one compound of the formula I

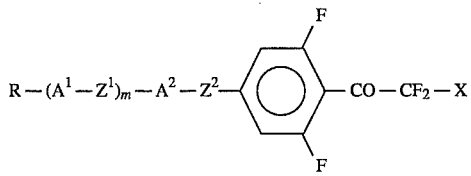

wherein R, $A^1$, $A^2$, $Z^1$, $Z^2$, X and m are as defined in claim 1.

9. Liquid-crystalline medium according to claim 8, characterized in that it additionally contains one or more compounds selected from the group consisting of the general formulae II, III and IV:

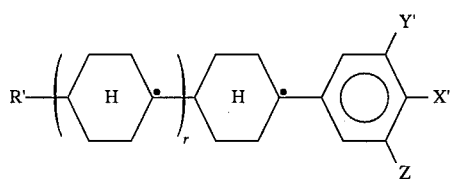

-continued

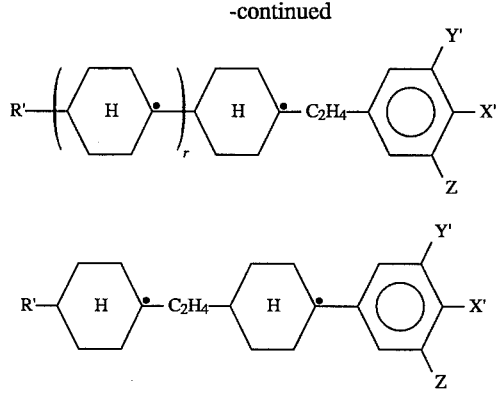

in which the individual radicals have the following meanings:

R': alkyl, oxaalkyl, fluoroalkyl or alkenyl, in each case having up to 7 carbon atoms, X': F, Cl, $CF_3$, $OCF_3$ or $OCHF_2$, Y' and Z: each, independently of another, H or F, and r: 0 or 1.

10. Liquid-crystal display element, characterized in that it contains a liquid-crystalline medium according to claim 8.

11. Electro-optical display element, characterized in that it contains, as dielectric, a liquid-crystalline medium according to claim 8.

* * * * *